US 6,670,337 B1

(12) United States Patent
Hellerqvist et al.

(10) Patent No.: US 6,670,337 B1
(45) Date of Patent: Dec. 30, 2003

(54) FACILITATION OF WOUND HEALING WITH CM101/GBS TOXIN

(75) Inventors: Carl G. Hellerqvist, Brentwood, TN (US); Michal Neeman, Mazkeret Batya (IL); Barbara D. Wamil, Nashville, TN (US); Rinat Abramovitch, Mordechai (IL)

(73) Assignees: Yeda Reaearch and Development Co., Ltd., Rehovot (IL); Vanderbilt University, Nashville, TN (US)

( * ) Notice: Subject to any disclaimer, the term of this patent is extended or adjusted under 35 U.S.C. 154(b) by 0 days.

(21) Appl. No.: 09/363,968

(22) Filed: Jul. 29, 1999

Related U.S. Application Data

(63) Continuation of application No. PCT/US98/01853, filed on Jan. 29, 1999.

(51) Int. Cl.$^7$ ........................ A01N 43/04; A61K 31/715
(52) U.S. Cl. ........................ 514/54; 536/55.1
(58) Field of Search ............................ 514/54; 536/55.1

(56) References Cited

U.S. PATENT DOCUMENTS

| | | |
|---|---|---|
| 4,242,326 A | 12/1980 | Sugawara et al. |
| 4,725,609 A | 2/1988 | Kull, Jr. et al. |
| 4,882,317 A | 11/1989 | Marburg et al. |
| 4,895,838 A | 1/1990 | McCluer et al. |
| 4,912,093 A | 3/1990 | Michaeli |
| 5,010,062 A | 4/1991 | Hellergvist |
| 5,145,676 A | 9/1992 | Fahey et al. |
| 5,160,483 A | 11/1992 | Postlethwaite et al. |
| 5,225,331 A | 7/1993 | Jennings et al. |
| 5,302,386 A | 4/1994 | Kasper et al. |
| 5,382,514 A | 1/1995 | Passaniti et al. |

FOREIGN PATENT DOCUMENTS

| | | |
|---|---|---|
| EP | 0 445 280 B1 | 9/1991 |
| WO | WO 91/04048 | 4/1991 |
| WO | WO 94/10202 | 5/1994 |
| WO | WO 94/20085 | 9/1994 |
| WO | WO 96/25171 | 8/1996 |
| WO | WO 97/41844 | 11/1997 |

OTHER PUBLICATIONS

The Merck Manual—17th Ed pp. 1074–1097 Baers, Ed., 1999.*
Abramovitch, R., et al., "Neovascularization Induced Growth of Implanted C6 Glioma Multicellular Spheroids: Magnetic Resonance Microimaging," *Cancer Research*, 55:1956–1962, (1995).
Arbiser, J.L., MD, Ph.D., et al., "Angiogenesis and the Skin: A Primer," *J. of the American Academy of Dermatology*, 34(3):486–497, (1996).
Augustin, H.G., et al., "Ovarian Angiogenesis: Phenotypic characterization of Endothelial Cells in a Physiological Model of Blood Vessel Growth and Regression," *Am. J. Pathol.*, 147(2):339–351, (1995).
Battegay, E.J., "Angiogenesis: Mechanistic Insights, Neovascular Diseases, and Therapeutic Prospects," *J. Mol. Med.*, 73:333–346, (1995).
Broadley, K.N., et al., "Monospecific Antibodies Implicate Basic Fibroblast Growth Factor in Normal Wound Repair," *Lab. Investigation*, 61(5):571–575, (1989).
Brown, L.F., et al., "Expression of Vascular Permeability Factor (Vascular Endothelial Growth Factor) by Epidermal Keratinocytes During Wound Healing," *J. Exp. Med.*, 176:1375–1379, (1992).
Brown, L.F., et al., "Increased Expression of Vascular Permeability Factor (Vascular Endothelial Growth Factor) in Bullous Pemphigoid, Dermatitis Herpetiformis, and Erythema Multiforme," *J. Invest. Dermatol.*, 104(5):744–749, (1995).
Brown, L.F., et al., "Overexpression of Vascular Permeability Factor (VPF/VEGF) and its Endothelial Cell Receptors in Delayed Hypersensitivity Skin Reactions," *J. Immunol.*, 154(6):2801–2807, (1995).
Dvorak, H.F., et al., "Vascular Permeability Factor/Vascular Endothelial Growth Factor: An Important Mediator of Angiogenesis in Malignancy and Inflammation," *Int. Arch. Allergy Immunol.*, 107:233–235, (1995).
Dvorak, H.F., et al., "Vascular Permeability Factor/Vascular Endothelial Growth Factor, Microvascular Hyperpermability, and Angiogenesis," *Am. J. Pathol.*, 146(5):1029–1039, (1995).
Ferrara, N., "The Role of Vascular Endothelial Growth Factor in Pathological Angiogenesis," *Breast Cancer Res. Treat.*, 36:127–137, (1995).
Ferrara, N., et al., "Vascular Endothelial Growth Factor, a Specific Regulator of Angiogenesis," *Curr. Opin. Nephrol. Hypertens.*, 5(1):35–44, (1996).
Folkman, J., "Angiogenesis in Cancer, Vascular, Rheumatoid and Other Disease," *Nature Medicine*, 1(1);27–31, (1995).
Folkman, J., et al., "Angiogenic Factors," *Science*, 2:442–448, (1987).
Folkman, J., "Diagnostic and Therapeutic Applications of Angiogenesis Research," *C. R. Acad. Sci. Paris, Sciences de la vie*, 316:914–918, (1993).

(List continued on next page.)

Primary Examiner—Gerald R. Ewoldt
(74) Attorney, Agent, or Firm—Cooley Godward LLP

(57) ABSTRACT

The method of the present invention provides a means for protecting a patient, including a transplant patient, from reperfusion injury by administering CM101 or GBS toxin isolated from Group B β-hemolytic Streptococcus bacteria. The present invention also includes a method to protect a tissue or organ against reperfusion injury in a transplant patient.

22 Claims, 2 Drawing Sheets

OTHER PUBLICATIONS

Gatenby, R.A., et al., "Suppression of Wound Healing in Tumor Bearing Animals as a Model for Tumor–Host Interaction: Mechanism of Suppression," *Cancer Research*, 50:7997–8001, (1990).

Hellerqvist, C.G., et al., "CM101 Induces a Complement–Activated Inflammatory Response Targeting Tumor Neovasculature," *Proceedings of the American Assoc. for Cancer Research*, Abstract #3328, (1996).

Hellerqvist, C.G., et al., "Cytokine Production in Cancer Patients Receiving the Anti–Neovascularization Drug CM–101," *Proceedings of ASCO*, Abstract #1592, vol. 14, (1995).

Hellerqvist, C.G., et al., "Studies on Group B β–Hemolytic Streptococcus I. Isolation and Partial Characterization of an Extra–Cellular Toxin," *Pediatr. Res.*, 15:892–898, (1981).

Hellerqvist, C.G., et al., "Antitmuor Effects of GBS Toxin: a Polysaccharide Exotoxin From Group B β–Hemolytic Streptococcus," *J. Canc. Res. Clin. Oncol.*, 120:63–70, (1993).

Hellerqvist, C.G. et al., "Early Results of a Phase I Trial of CM101 in Cancer Patients," *Proceedings of the American Assoc. of Cancer Research Annual Meeting*, 36:224, (1995) Abstract.

Hellerqvist, C.G., et al., "Molecular Basis for Group B β–Hemolytic Streptococcal Disease," *Proc. Natl. Acad. Sci. USA*, 84:51–55, (1987).

Hellerqvist, C.G., et al., "Preliminary Results of a Phase I Trial of CM101 in Cancer Patients," *J. Cell. Biochem.*, 19B:26 (1995) Abstract.

Herblin, W., et al., "Inhibition of Angiogenesis as a Strategy for Tumor Growth Control," *Molecular and Chemical Neuropathology*, 21:329–336, (1994).

Jennings, H.J., et al., "Structural Determination and Serology of the Native Polysaccharide Antigen of Type–III Group B–Streptococcus," *Can. J. of Biochem.*, 58(2):112–120, (1980).

Kim, K.J., et al., "Inhibition of Vascular Endothelial Growth Factor–Induced Angiogenesis Suppresses Tumour Growth in Vivo," *Nature*, 362:841–844, (1993).

Klagsbrun, M., et al., "Regulators of Angiogenesis," *Annu. Rev. Physiol.*, 53:217–239, (1991).

Kovacs, E.J., et al., "Fibrogenic Cytokines and Connective Tissue Production," *The FASEB Journal*, 8:854–861, (1994).

Moses, M.A., et al., "Identification of an Inhibitor of Neovascularization From Cartilage," *Science*, 248:1408–1410, (1990).

Murthy, S.M., et al., "The Influence of Surgical Trauma on Experimental Metastasis," *Cancer*, 64(10):2035–2044, (1989).

Murthy, S.M, et al., "Inhibition of Tumor Implantation at Sites of Trauma by Plasminogen Activators," *Cancer*, 68(8):1724–1730, (1991).

Ondrick, K., Ph.D., et al., "Angiogenesis," *Clinics in Podiatric Medicine and Surgery*, 9(1):185–203, (1992).

Ono, M., et al., "Induction of Human Microvascular Endothelial Tubular Morphogenesis by Human Keratinocytes: Involvement of Transforming Growth Factor–α," *Biochem. Biophys. Res. Commun.*, 189(2):601–609.

Parkinson, D.R., "Present Status of Biological Response Modifiers in Cancer," *The Amer. J. of Medicine*, 99(6A Suppl.),:54S–56S, (1995).

Pierce, G.F., et al., Pharmacologic Enhancement of Wound Healing, *Annu. Rev. Med.*, 46:467–481, (1995).

Plate, K.H., et al., "Molecular Mechanisms of Developmental and Tumor Angiogenesis," *Brain Pathol.*, 4:207–218, (1994).

Polverini, P.J., "The Pathophysiology of Angiogenesis," *Crit. Rev. Oral Biol. Med.*, 6(3):230–247, (1995).

Quinn, T.E., et al., "CM101, a Polysaccharide Antitumor Agent, Does Not Inhibit Wound Healing in Murine Models," *J. Cancer Res. Clin. Oncol.*, 121:253–256, (1995).

Rubin, E., et al., *Pathology*, Lippincott, publ., pp. 75–95, (1994).

Sato, N., et al., Actions of TNF and IFN–γ on Angiogenesis In Vitro, *The J. of Investigative Dermatology*, 95(6 Suppl.):85S–89S, (1990).

Schackert, H.K., et al., "Development of an Animal Model to Study the Biology of Recurrent Colorectal Cancer Originating From Mesenteric Lymph System Mestastases," *Int. J. Cancer*, 44:177–181, (1989).

Senger, D.R., et al., "Vascular Permeability Factor, Tumor Angiogenesis and Stroma Generation," *Invasion Metastasis*, 14:385–394, (1994–1995).

Senger, D.R., et al., "Vascular Permeability Factor (VPF, VEGF) in Tumor Biology," *Cancer and Metastasis Reviews*, 12:303–324, (1993).

Shah, M., et al., "Control of Scarring in Adult, Wounds by Neutralising Antibody to Transforming Growth Factor β," *The Lancet*, 339:213–214, (1992).

Shweiki, D., et al., "Induction of Vascular Endothelial Growth Factor Expression by Hypoxia and by Glucose Deficiency in Multicell Spheroids: Implications for Tumor Angiogenesis," *Proc. Natl. Acad. Sci. USA*, 92:768–772, (1995).

Shweiki, D., et al., "Vascular Endothelial Growth Factor Induced by Hypoxia May Mediate Hypoxia–Initiated Angiogenesis," *Nature*, 359:843–845, (1992).

Stein, I., et al., "Stabilization of Vascular Endothelial Growth Factor mRNA by Hypoxia and Hypoglycemia and Coregulation With Other Ischemia–Induced Genes," *Molecular and Cellular Biology*, 15(10):5363–5368, (1995).

Stout, A.J., et al., "Inhibition of Wound Healing in Mice by Local Interferon /β Injection," *Int. J. Exp. Pathol.*, 74:79–85, (1993).

Turco, S.J., "Intravenous Admixtures," *Remington's Pharmaceutical Sciences*, 18th ed., chapter 85:1570–1580, Mach Publ., (1990).

Wamil, B.D., et al., "Leukocyte Activation in Response to CM104 Treatment of Cancer Patients," *Proceedings of the American Assoc. for Cancer Research*, Abstract #3329, (1996).

* cited by examiner

FACILITATION OF WOUND HEALING WITH CM101/GBS TOXIN

CROSS-REFERENCE TO RELATED APPLICATIONS

This application is a continuation of PCT/US98/01853, filed Jan. 29, 1998, published as WO 98/32453 on Jul. 30, 1998, which claims priority to U.S. Ser. No. 08/791,763, filed Jan. 29, 1997, now U.S. Pat. No. 5,858,991, issued Jan. 12, 1999.

TECHNICAL FIELD

This invention relates to the facilitation of wound healing in patients, by minimizing scarring and accelerating healing. This invention also relates to the reduction of wound-related tumor progression.

BACKGROUND

The normal process of healing a skin wound that has been surgically induced or is the result of trauma involves formation of a blood clot and, often, a scab. More particularly, first intention, or primary healing, generally occurs at clean incisions, whereas second intention, or secondary healing, occurs where wound edges are far apart. The protein fibrin holds the edges of the skin surrounding the wound together and the scab seals the wound and staves off infection. While an inflammatory response brings increased numbers of blood cells to the area to aid in the repair process, epithelial tissue regenerates and capillaries grow from blood vessels at the edges of the wound. The capillaries revascularize the area of the wound and contribute to the formation of granulation tissue which, in turn, causes scarring.

Granulation tissue begins to form in the wound site and fills the site approximately five days after wound induction. Granulation tissue contains new collagen, fibroblasts, new blood vessels and inflammatory cells, especially macrophages (E. Rubin and J. L. Farber, *Pathology*, Lippincott, publ., pp. 85–95 (1994)). After seven to ten days, the wound has regained only 10% of the tissue's original strength.

Secondary healing causes a greater inflammatory response and more granulation tissue is formed. In addition, contraction of the wound, resulting from contraction of the fibroblasts of the granulation tissue, brings the edges of the wound together to speed the healing process, but sometimes contributes to disfiguring and debilitating scars. Additionally, excessive deposition of extracellular matrix leads to the formation of keloids, or hypertrophic scars, which are irregularly-shaped, elevated scars that tend toward progressive enlargement.

Angiogenesis is generally believed to be a necessary feature of repair (Kovacs, E. et al., *Fibrogenic cytokines and connective tissue production*, FASEB J., 8:854–861 (1994). Numerous growth factors and cytokines, secreted first by platelets in response to coagulation and then by macrophages in response to hypoxia and lactic acidosis, stimulate angiogenesis (Shah, M. et al., *The Lancet*, 339:213–214 (1992)). Angiogenesis generally becomes visible at a microscopic level about four days after injury but begins two or three days earlier when new capillaries sprout out of pre-existing venules and grow toward the injury in response to chemoattractants released by platelets and macrophages. In primarily closed wounds, sprouting vessels soon meet counterparts migrating from the other side of the wound and blood flow across the wound is reestablished. In unclosed wounds, or those not well closed, the new capillaries fuse only with neighbors migrating in the same direction, and a large amount of granulation tissue is formed instead.

In normal wound healing, the tissue surrounding a wound undergoes a degree of hypoxia and a concomitant increase in secretion of vascular endothelial growth factor, or VEGF, typically occurring one to two days following injury (Brown, L. F. et al., *Expression of VPF (VEGF) by epidermal keratinocytes during wound healing*, J. Exp. Med., 176:1375–79 (1992)). VEGF stimulates the rapid proliferation of blood vessel endothelial cells which results in the formation of densely sprouting capillaries. This rapid hypoxia-induced, VEGF-driven capillary formation stimulates infiltration of inflammatory cells and leads eventually to scarring.

While inflammation causes scarring, inflammation is also beneficial. Inflammatory cells release growth signals and lytic enzymes that are very important for repair. In fact, patients who receive anti-inflammatory agents often experience impaired healing due to inadequate inflammation at the site of a wound.

An important aspect of wound repair is the time involved. The rate at which a wound heals has implications for the prevention of infection and improvement of the overall health of the patient. Rapid, even healing without excessive contraction is a desirable result from a medical and cosmetic standpoint.

Furthermore, it is a recognized clinical phenomenon that surgery in a tumor patient may lead to tumor progression if the site of the surgical incision is in proximity to the site of the tumor. In addition, the surgical incisions show high susceptibility to metastatic implantation. (Murthy et al., *Cancer*, 64:2035–2044 (1989); Murthy et al., *Cancer*, 68:1724–1730 (1991); Schackert, H. K. et al., *Int. J. Cancer*, 44:177–81 (1989)). The stimulatory effect of wounds on tumors is manifested as accelerated growth of residual tumor near the site of surgical intervention, as well as an increased probability of metastatic implantation at the site of surgery. Furthermore, wounds located at the site of a tumor regularly fail to heal (Gatenby, R. A. et al., *Suppression of wound healing in tumor bearing animals*, Cancer Research, 50:7997–8001 (1990)). Persistent wounds that continuously accelerate tumor progression may be a frequent side effect of surgical interventions associated with cancer therapy. Therefore, deciding whether to operate on a tumor patient is often a difficult decision in which the benefits of surgery must be compared to the risks of worsening a cancer patient's overall condition.

It is an object, therefore, of the present invention to provide a method of preventing or minimizing scar formation during the wound healing process.

Another object of the present invention is to provide a method of accelerating the rate at which a wound heals.

A further object of the present invention is to provide a method of facilitating wound healing in tumor patients and minimizing the likelihood of tumor progression.

SUMMARY OF THE INVENTION

The method of the present invention provides for treating a patient having a wound by administering CM101, a generally nontoxic polysaccharide isolated from group B β-hemolytic Streptococcus (GBS) bacteria, to minimize scarring and to accelerate wound healing. The invention finds use in treatment of surface as well as internal wounds.

Another aspect of the present invention is a method for treating a keloid by excising the keloid and administering CM101.

The present invention also provides a method of minimizing the likelihood of tumor progression, i.e. wound-induced tumor proliferation or metastatic implantation by administration of CM101 before, during and/or after surgery or other induction of a wound in a tumor patient.

An article of manufacture including GBS toxin, and particularly CM101, along with instructions for treatment, and a method of making the article are also disclosed.

DETAILED DESCRIPTION OF THE INVENTION

Figure 1:
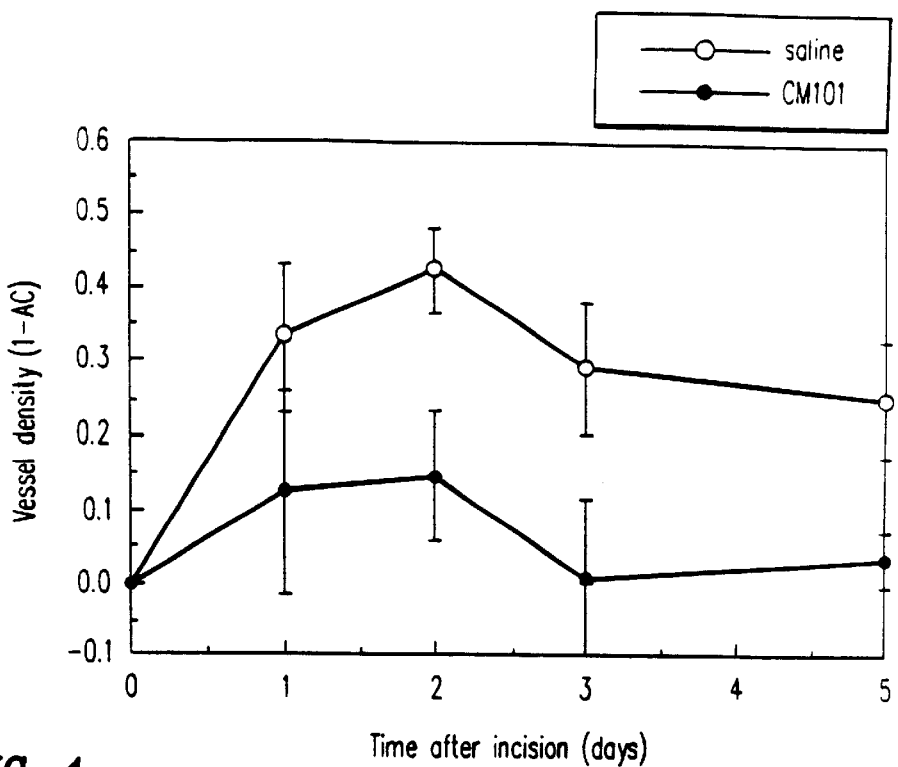
FIG. 1 graphs vessel density around wounds in tumor-free mice treated with CM101 or saline solution.

This invention is based in part on the discovery that GBS toxin, and particularly CM101, facilitates wound healing by promoting rapid healing with minimal scarring. CM101 presumably produces these beneficial effects by diminishing the rapid hypoxia-related VEGF-driven neovascularization that contributes to the scarring associated with wound healing. This mechanism of action also contributes to rapid, even healing of wounds in tumor patients, thus reducing the likelihood of tumor proliferation or metastatic implantation at the site of surgery or other wounding.

CM101, a GBS toxin, is a polysaccharide molecule isolated from group B β-hemolytic Streptococcus (GBS) bacteria. Specifically, pathogenic group B β-hemolytic streptococcus produces a polysaccharide exotoxin. This exotoxin is the putative agent for GBS pneumonia or "early onset disease" in neonatal humans. These newborn infants may suffer from sepsis, granulocytopenia, and respiratory distress, i.e. pulmonary hypertension and proteinaceous pulmonary edema (Hellerqvist, C. G. et al., *Studies on group B β-hemolytic streptococcus I. Isolation and partial characterization of an extra-cellular toxin.*, Pediatr. Res., 12:892–898 (1981)). It is believed that receptors for CM101 are present primarily on the lungs of newborns, making them susceptible to early onset disease, but that lung cells lose CM101 receptors approximately four to seven days after birth. Thus, despite the harmful effects on neonates exposed to GBS, CM101 is not known to cause toxicity in older humans.

Isolated CM101 has been shown to have toxic effects on sheep experimental models that mimic GBS infant pneumonia (Hellerqvist, C. G. et al., *Studies on group B β-hemolytic streptococcus I. Isolation and partial characterization of an extra-cellular toxin.*, Pediatr. Res., 12:892–898 (1981)). In the sheep model for neonatal early onset disease, GBS toxin causes pulmonary hypertension, increased pulmonary vascular permeability, granulocytopenia, and pulmonary sequestration of granulocytes.

CM101 has a molecular weight of approximately 300,000 Daltons and comprises N-acetyl-galactosamine, N-acetyl-glucosamine, glucose, galactose, and mannose residues, in an approximate 1:1:1:3:1 ratio. Carboxylic acid residues are also believed to be integral parts of the molecule. Repeating active epitopes most likely play an important role in the pathophysiological response to CM101 by crosslinking receptors on target endothelium (Hellerqvist, C. G. et al., *Early Results of a Phase I Trial of CM101 in Cancer Patients.*, Proceedings of the American Association of Cancer Research Annual Meeting, 36:224 (1995)).

A method of preparation of a GBS toxin is provided in U.S. Pat. No. 5,010,062. Preferably, however, the CM101 is purified according to the method taught in International Application No. PCT/US97/17535, incorporated herein by reference.

Starting material for isolating CM101 for use in the method of the present invention may be obtained by culturing strains of Group B β-hemotytic Streptococcus bacteria that have recently infected or are capable of infecting newborn infants. Isolates of such strains may be obtained from the blood or cerebrospinal fluid of infected infants.

GBS toxin as used herein is defined as any fraction or component isolated from natural or lysed GBS bacteria, or derived from media supernatants of lysed and/or autoclaved GBS bacteria, and which has a biological activity evidenced by induction of respiratory distress in the sheep assay (Hellerqvist, C. G. et al., *Studies on group B β-hemolytic streptococcus I. Isolation and partial characterization of an extra-cellular toxin.*, Pediatr. Res., 12:892–898 (1981)) or activation of complement and binding to neovasculature as demonstrated by a peroxidase-antiperoxidase (PAP) assay of a tumor tissue specimen (Hellerqvist, C. G. et al., *Anti-tumor effects of GBS toxin: a polysaccharide exotoxin from group B β-hemolytic streptococcus*, J. Canc. Res. Clin. Oncol., 120:63–70 (1993); and Hellerqvist, C. G. et al., *Early Results of a Phase I Trial of CM101 in Cancer Patients.*, Proceedings of the American Association of Cancer Research Annual Meeting, 36:224 (1995)). GBS toxin also means any natural or synthetic polysaccharide with the same structure or function as any GBS-derived molecule with the aforementioned activity.

Substantially pure GBS toxin means a preparation in which GBS toxin is greater than 40% pure (e.g., present in a concentration of at least about 40% by weight), preferably at least approximately 60% pure, more preferably at least approximately 90% pure, and most preferably at least approximately 95% pure. The purity of GBS toxin is discussed in greater detail in International Application No. PCT/US97/17535. The dosages described herein are for 95% pure GBS toxin. Dosages of lower purity GBS toxin should be altered accordingly.

One aspect of the present invention is a method of treating a patient having a wound by administering a GBS toxin, e.g. CM101, in an amount sufficient to reduce scarring and/or to accelerate wound healing. Determination of the reduction of scarring and/or the acceleration of healing may be performed by a variety of methods including, but not limited to, visual observation, measurement of vessel density at the site of the wound, e.g., by magnetic resonance imaging, measurement of the amount and/or rate at which granulation tissue is formed, and measurement of skin tensile strength at the site of the wound.

The CM101 or other GBS toxin is preferably combined with a pharmaceutically acceptable carrier and administered to a patient systemically.

The carrier is preferably one that is readily mixed with CM101 to form a composition that is administrable by intravenous (IV) means. Thus, the carrier is preferably saline, which may have other pharmaceutically acceptable excipients included to ensure its suitability for intravenous administration. The resulting composition will be sterile and will have acceptable osmotic properties. In general, a suitable IV formulation is prepared in accordance with standard techniques known to one of skill in the art. For example, Chapter 85 entitled "Intravenous Admixtures" by Salvatore J. Turco in the Eighteenth Edition of *Remington's Pharmaceutical Sciences,* Mach Publishing Co. (1990), incorporated herein by reference, provides standard techniques for preparing a pharmaceutically acceptable IV composition useful in accordance with this invention. Other dosage forms to administer CM101 may also be used. As an alternative to systemic administration, CM101 may be administered locally to a wound site. Administration of CM101 to the patient may occur before, during, and/or after infliction of a wound by surgery or trauma. Preferably, CM101 is administered within an appropriate temporal window following the wounding. Administration of CM101 soon after infliction of the wound is most preferred. For example, administration within 1 day, or preferably within six hours is best.

The amount of CM101 that is administered to a patient to reduce scarring or accelerate the rate of wound healing is an amount that is sufficient to reduce the amount or rate of granulation tissue formation at a wound site, or that is sufficient to reduce vascularization, and particularly vessel density, at a wound site. A preferred dosage range is 1 to 100 $\mu$g/kg body weight. A more preferred dosage range, however, is 1 $\mu$g/kg to 50 $\mu$g/kg body weight, and most preferred is a dosage in the range of 1 $\mu$g/kg to 25 $\mu$g/kg. It will be understood, however, that the specific dose level for any particular patient will depend on a variety of factors including the age, body weight, general health, sex, diet, and severity of the wound. Each dosage is preferably administered in an infusion of up to 120 minutes, with 5 to 60 minutes being the preferred duration range, and 5 to 30 minutes being the most preferred dosage range. Once weekly treatment is preferred, and is likely to be all that is necessary for evidence of results.

CM101 treatment inhibits scarring and accelerates healing of wounds in various types of tissues and is appropriate for wounds of various depths. The treatment of the present invention is preferably used in conjunction with suturing of muscle tissue or some other known tissue manipulation for wounds which are deep or in which the edges of the tissue are not close together. Scarring at the level of the epidermis as well as internal scarring is reduced by the method of the present invention. A scar as used herein is an irregularity of the skin or other tissue formed from connective tissue replacement of tissue, especially tissue damaged by a wound process. An adhesion may also be considered a scar in this context. A wound as used herein is injury or damage wherein the skin or other tissue is adversely affected, particularly wherein the skin or other tissue is torn, pierced, cut, or broken.

Additionally, the present invention may be used to treat reperfusion injuries due to surgical wounds or traumatized wounds. For instance, blood flow to a part of the body may be temporarily occluded, as by clamping, during a surgical procedure. After removal of the occlusion, reperfusion into a previously ischemic area may result in a reperfusion injury to the tissue, especially inside the blood vessel. Reperfusion injury is a major contributor to organ failure and organ rejection in transplant surgery. CM101 may be administered to the patient before occlusion to minimize damage caused by ischemia and reperfusion. CM101 may also be administered after the occlusion has occurred. Restenosis, often resulting from scarring within a blood vessel that leads to stricture of the vessel lumen, is also advantageously treated by the method of the present invention. Further, the invention may be used to minimize the likelihood of formation of adhesions, such as the type which sometimes occurs as a result of abdominal surgery. Clearly, the method may be used in specific types of surgery, such as plastic or cosmetic surgery, implantation, reconstruction, transplantation, bypass operations, and balloon angioplasty where improved wound healing is critical and scarring is particularly problematic. Many of these procedures are believed to involve hypoxia-induced neovascularization or angiogenesis.

CM101 is especially useful in the treatment of patients having keloids. Normally, surgery to excise these overgrown scars is unsuccessful, because they continually return in a larger and more unsightly form. The present invention teaches a method of treatment whereby surgery to excise the keloid and create a fresh wound is immediately followed by administration of CM101 to allow for healing with minimal scarring.

As stated above, the stimulatory effect of wounds on tumors is a recognized clinical phenomenon that is manifested as accelerated growth of the residual tumor near the site of surgical intervention, as well as an increased probability of metastatic implantation at the site of surgery. The present invention also includes administration of CM101 to surgery patients with tumors in order to facilitate wound healing and to minimize metastatic implantation and tumor proliferation. Treatment for wound healing in surgery patients with tumors includes prevention or reduction of the likelihood of occurrence, and reduction of any tumor that has moved to the wound site.

Clearly, administration of CM101 pre-surgery to reduce scarring and accelerate wound healing has great utility and will favorably impact the medical community. Similarly, the administration of CM101 to a patient having a wound resulting from unexpected injury has great utility in facilitating healing of the wound.

Without limitation to a particular theory, it is believed that GBS toxin, and specifically CM101, plays an important role in allowing wounds to heal at an accelerated rate and with minimal scarring because it interferes with the hypoxia-induced, VEGF-driven angiogenesis that results in tissue granulation and scarring, but not with physiological blood vessel repair processes which are necessary for the wound to heal. Angiogenesis is believed to involve dedifferentiation of endothelial cells in response to upregulation of VEGF under hypoxic conditions, ultimately leading to the rapid formation of densely-sprouting capillaries. On the other hand, physiological neovascularization is believed to be a basic repair mechanism involving proliferation of existing endothelial cells after the disruption of contact inhibition resulting from infliction of a wound. Because CM101 allows physiological repair mechanisms to proceed, but interferes with pathological angiogenesis, it is an extremely useful compound for the beneficial treatment of wounds. The further suggestion is that CM101 opsonizes, by complement C3 activation, the budding capillary sprout, thereby inhibiting inflammatory angiogenesis necessary for scarring. VEGF-driven angiogenesis is also believed to be at work in reperfusion injury-type wounds, thus administration of CM101 is effective in preventing such injuries.

Previous work by some of the inventors of the present application utilized GBS toxin as an anticancer agent in the treatment of tumors. Particularly, U.S. Pat. No. 5,010,062 to Hellerqvist and the corresponding European Patent No. EP 0 445 280 B1 teach a method of at least partially inhibiting vascularization of a developing solid tumor by parenterally administering to a patient GBS toxin in an amount effective for inhibition.

The previous work led to investigation of the effect of GBS toxin, and particularly CM101, on wound site vasculature. The conclusion of the early investigation was that CM101 had no effect on wound healing. Specifically, Quinn, T. E. et al., *J. Cancer Res. Clin. Oncol.* 121:253–6 (1995) utilized a polyvinyl alcohol (PVA) sponge implantation technique in mice as a model for wound healing and a carmine dye infusion method to measure new vessel formation. In that study, there was no significant difference in the level of vasculature exhibited by mice treated with CM101 or control Dextran. This was true for both normal and tumor-bearing mice. These results indicated that CM101 had no significant effects on the neovasculature of healing wounds as measured by the sponge model. Thus, early studies of the effects of CM101 on wound healing lead one away from the present invention.

Magnetic resonance imaging (MRI) is useful for visualizing vascularization and providing a relative measure of vessel density. This technique has been used to visualize wound-tumor interactions in vivo in nude mice (Abramovitch R., Meir G. and Neeman M., *Neovascularization induced growth of implanted C6 glioma multicellular spheroids: magnetic resonance microimaging, Cancer Res.,* 55:1956–1962 (1995)) and to demonstrate that wounds influence tumor progression indirectly by stimulating tumor neovascularization and directly by inducing tumor cell proliferation. In the course of these observations, wounds located at the site of a tumor did not heal.

Most antiangiogenic or antineovasculature therapies (Broadley. K. N. et al., *Lab. Investigation,* 61(5):571–575 (1989); Stout, A. J. et al., *Int. J. Exp. Pathol.,* 74(1):79–85 (1993); Pierce, G. F., *Annu. Rev. Med.,* 46:467–481(1995)), with the exception of CM101, inhibit wound healing and therefore cannot be used to inhibit the stimulatory effect of surgery on tumor growth. It was previously demonstrated that CM101 inhibits tumor neovascularization, (U.S. Pat. No. 5,010,062) and previous investigators concluded that CM101 has no significant effect on neovascularization of wounds (Quinn T. E., Thurman G. B., Sundell A. K., Zhang M., and Hellerqvist C. G., *CM*101, *a polysaccharide antitumor agent, does not inhibit wound healing in murine models, J. Cancer Res. Clin. Oncol.,* 121:253–256 (1995)). The present invention, by contrast, teaches that CM101 increases the rate of wound healing, decreases scarring and further, in cancer patients, acts to inhibit the proliferative effect of wounds on tumors.

Another aspect of the present invention is an article of manufacture, such as a kit, and a method for making the article of manufacture. The article includes a pharmaceutical composition comprising a GBS toxin, and particularly CM101, and a pharmaceutically acceptable carrier. The pharmaceutical composition may be placed in a suitable container, as is well known in the art. Also included are instructions for treatment of patients according to the methods of the present invention.

The invention now being generally described may be better understood by reference to the following examples, which are presented for illustration only and are not to be construed as limitations on the scope or spirit of the present invention.

EXAMPLES

Example 1
CM101 Facilitates Wound Healing in Tumor-free Subjects

The effect of CM101 on wound healing was determined in CD-1 nude mice lacking tumors. The wounds were produced by fine surgical scissors and consisted of 4 mm full thickness skin incisions. A sterile adhesive bandage (Tegaderm™, USA) was used to cover each wound.

On day 0 of the experiment, mice were intravenously administered 240 µg/kg CM101 or saline and wounded. New vessel formation at each wound site was assessed using magnetic resonance microimaging (MRI). Magnetic resonance images were obtained on days 0, 1, 2, 3, and 5.

MRI experiments were performed on a horizontal 4.7 T Biospec spectrometer (Bruker, Germany) spectrometer using a 2 cm surface radio-frequency coil. Gradient echo images (slice thickness of 0.5 mm, TR 100 ms, 256×256 pixels, in plane resolution of 110 µm) were acquired with echo times of 10.5 and 20 ms. Growth of the capillary bed was reflected by reduction of the mean intensity at a region of interest of 1 mm surrounding the incision. Angiogenic contrast (AC) was defined as the ratio of the mean intensity at a region of interest of 1 mm surrounding the incision to the mean intensity of a distant tissue. Apparent vessel density is given as 1-AC. Each anesthetized mouse was then placed supine on an MRI device with the incision site located at the center of the surface coil, and MRI images were recorded for 1 hour.

FIG. 1 shows the vessel density measurements by MRI over the time course of the experiment. As shown in FIG. 1, wounds in saline-treated control mice exhibited intense neovascularization near the wound. This neovascularization peaks on the second day after injury. In comparison, CM101-treated mice have a severely diminished level of neovascularization around the wounds.

Example 2
CM101 Facilitates Wound-healing in Tumor-bearing Subjects

The effect of CM101 on neovascularization of wounds was tested using mice implanted with glioma spheroids. A single C6 glioma spheroid (about 800 µm in diameter) was implanted subcutaneously to the lower back of each of 6 male CD1-nude mice (Abramovitch R., Meir G. and Neeman M., *Neovascularization induced growth of implanted C6 glioma multicellular spheroids: magnetic resonance microimaging, Cancer Res.,* 55:1956–1962 (1995)).

Eight days later, on day 0 of the experiment, the mice were anesthetized with a intraperitoneal injection of 75 µg/g Ketamine and 3 µg/g Xylazine. The mice were injected through the tail vein with physiological saline containing 0, 60, 120, or 240 µg/kg CM101. Neovascularization at the wound site was assessed using magnetic resonance microimaging (MRI), as described in Example 1. Each anesthetized mouse was placed supine on the MRI device with the tumor located at the center of the surface coil, and MRI images were recorded for one hour.

After 1 hour of observation and MRI data recording, the mice were wounded by a 4 mm cutaneous incision 5–10 mm from the tumor. As before, the wounds were made through 4 mm full thickness of tissue by fine surgical scissors and were covered with a sterile adhesive bandage (Tegaderrnm™, USA). Subsequent MRI images of neovascularization were taken on days 2, 5, 7, and 13.

Figure 2:
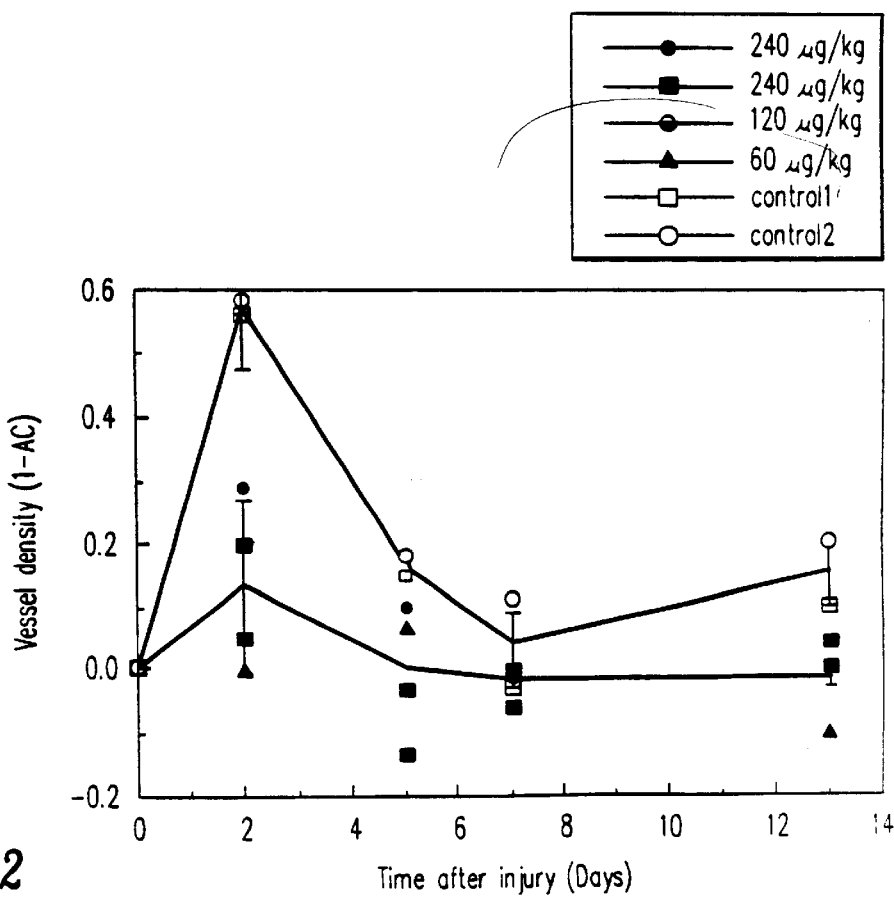
FIG. 2 graphs vessel density around wounds in tumor-bearing mice treated with CM101 or saline solution.

Wound healing in mice with gliomas was improved by a single injection of CM101. Mice treated with CM101 displayed approximately six-fold reduced vessel density at the edges of the wound 2 days after injury, as seen in FIG. 2. The initial wave of massive neovascularization following wounding was inhibited in CM101-treated mice, but this inhibition did not impair wound healing. In fact, at 24 and 48 hours after injury, wounds were almost undetectable externally in mice treated with CM101, whereas control mice more clearly showed the wound. Furthermore, compared to saline-treated control mice, CM101 treated, tumor-bearing mice had almost no detectable scar 13 days after the injury.

Thus, in tumor-bearing subjects treatment with CM101 severely diminishes the massive neovascularization that surrounds the wound on days 1–2 after injury, accelerates wound healing, and minimizes scarring.

Example 3
CM101 Treatment Promotes Improved Incision Healing

Visual observation of wounds also provides evidence of the benefits of CM101 treatment. Two mice were wounded as in the previous examples. CM101 was then administered intravenously at a 240 µg/kg dosage in saline to one mouse. Saline was administered to the control mouse using the same procedure.

Visual observation of the wound site 48 hours post-incision and post-CM101 treatment confirmed that the wound site is barely detectable. By contrast, a comparable wound site in the control animal viewed at the same time point shows clear evidence of wounding. The experimental animal also presented little evidence of scarring as compared to the control animal at a later time point.

Example 4
CM101 Accelerates Wound Healing

Wound disruption strength, or tissue tensile strength across a wound, was evaluated with CD1-nude mice. Full thickness skin incisions were made on the right lumbar region followed by intravenous injection with CM101 at 30 and 60 µg/kg or saline. The force needed to disrupt the wound was measured at 40 hours and 7 days after incision. Animals treated with CM101 demonstrated significant increases relative to controls in the strength of the healing wounds.

Figure 3:
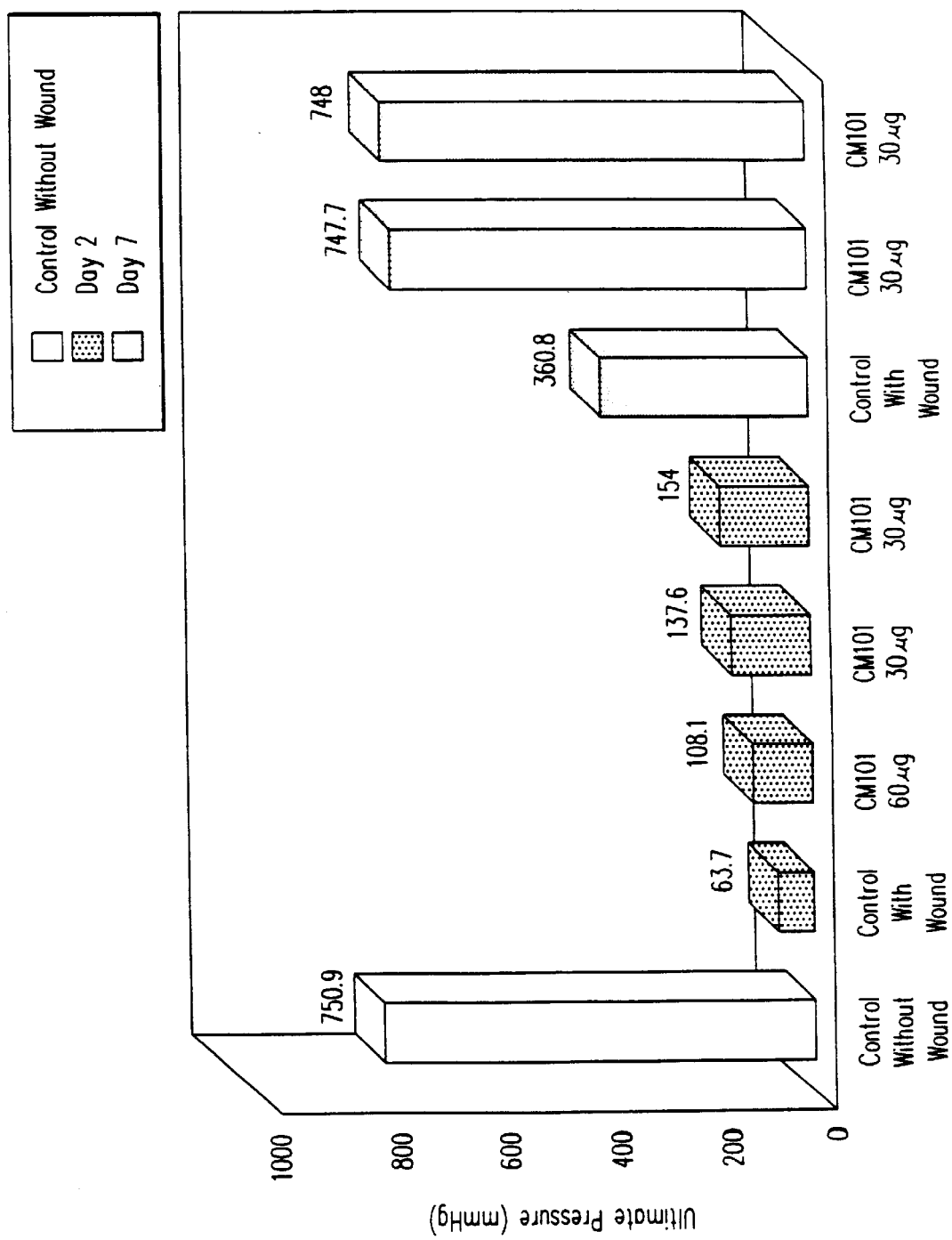
FIG. 3 presents a graphic representation of the effect of CM101 on the recovery of skin strength after wounding.

Six millimeter incisions were made on day 0. Tensile strength was measured day 2 and day 7 by applying vacuum (Dimensional Analysis Systems, Inc.) over the wound and registering the movement of two small dots of reflective material applied on each side of the wound by a video camera emitting infrared light. FIG. 3 shows that by 2 days, there is a measurable difference between CM101 treated and control wounds. By 7 days, there is no visible scar tissue in the CM101 treated mice and the tissue has the strength of uninjured tissue. In contrast, untreated wounds were 50% less strong than CM101 treated wounds.

Example 5
CM101 Reduces the Effect of Wound-induced Tumor Progression

Twenty-four CD-1 nude mice carrying subcutaneous C6 glioma tumors of at least 5 mm diameter are prepared.

The effects of CM101 on tumor proliferation and metastatic implantation is tested using mice implanted with glioma spheroids. A single C6 glioma spheroid (at least 5 mm in diameter) is implanted subcutaneously to the lower back of each of 24 male CD1-nude mice (Abramovitch R., Meir G. and Neeman M., *Neovascularization induced growth of implanted C6 glioma multicellular spheroids: nagnetic resonance microimaging, Cancer Res.,* 55:1956–1962 (1995)).

Eight days later, on day 0 of the experiment, one group of mice (n=8) receive a 4 mm cutaneous incisional injury proximal to the tumor (within 3 mm of the tumor's edge), a second group of mice (n=8) receive a 4 mm cutaneous incisional injury at a location remote from the tumor (more than 10 mm from the tumor's edge), and a control group of mice (n=8) are left without a wound. On the same day, the mice receive treatments of 0, 60, 120 or 240 µg/kg CM101 (in each group described above, two mice receive a particular concentration of CM101).

For two weeks, tumor growth in situ, tumor implantation at the site of wound, and neovascularization at the wound site are assessed using magnetic resonance microimaging (MRI), as described in Example 1. At the end of two weeks, the mice are sacrificed and the tissue surrounding the tumor and wound are formalin-fixed for histological analysis of wound healing and tumor morphology.

In animals with wounds proximal to tumors, CM101 treatment reduces tumor proliferation into the site of the wound. Similarly, CM101 inhibits metastatic tumor implantation at the wound site in animals with tumors distant from wounds.

Example 6
CM101 is Effective Against Reperfusion Injury

The ability of CM101 to guard against reperfusion injury was tested using established animal models (Han et al., *Sialyl Lewis$^x$ Oligosaccharide Reduces Ischemia-Reperfusion Injury in the Rabbit Ear, J. of Immunol.,* 155 (8):401 1–4015 (1995), Missawa et al., *Role of Sialyl Lewis$^x$ in Total Hepatic Ischemia and Reperfusion, J. of the American College of Surgeons,* 182:251–256 (1996), Lopez-Neblina et al., *Mechanism of Protection of Verapamil by Preventing Neutrophil Infiltration in the Ischemic Rat Kidney, J. Surg. Res.,* 61(2):469–472 (1996). In both the ear model and the kidney model, the CM101-treated organ exhibited significantly less damage than did the untreated organ.

Mouse Ear Model

Balb/c mice were injected intravenously with either phosphate-buffered saline (n=10) or 60 µg/kg CM101 prepared in phosphate-buffered saline (n=10). Following injection, in each mouse, the artery supplying blood to one ear was clamped for a period of 60 minutes. At the end of the time period, the clamped ear had lost color, showing the effectiveness of the occlusion. After removal of the clamp, the ear of each mouse was allowed to reperfuse normally. The mice were maintained at a stable ambient temperature of 24° C. throughout the experiment. After six hours, the ears of all mice were visually examined directly and under a microscope (100×). Measurements of swelling were also performed using standard calipers.

The ear that had been subject to clamping was examined in each saline-treated mouse and showed swelling and significant vascular leakage indicated by hemorrhage and inflammatory infiltration as compared to the other ear of the mouse, which had not been subject to clamping. By contrast, the reperfused ear of each CM101-treated mouse showed no significant difference from the unclamped control ear of the same mouse.

Mouse Kidney Model

Anesthetized Balb/c mice were opened and the blood flow to one kidney was blocked by clamping. After clamping of the one kidney, either phosphate-buffered saline (Subgroup A) or 60 µg/kg CM101 in phosphate-buffered saline (Subgroup B) was infused intravenously through the tail vein of each mouse. Five minutes after the infusion, the blood flow to the other kidney of each animal was clamped. Both clamps were removed from each mouse simultaneously after the designated occlusion time period and reperfusion was allowed to proceed normally. A stable ambient temperature of 24° C. was maintained. After the designated reperfusion period, each mouse was sacrificed and examined. The first group of mice {6 saline-treated mice (Group 1A) and 6 CM101-treated mice (Group 1B)} had the blood flow to their kidneys occluded by clamping for 30 minutes and reperfusion was allowed to proceed for 2 hours. The second group {6 saline-treated mice (Group 2A) and 6

CM101-treated mice (Group 2B)} were subject to a 45 minute occlusion period and a 5 hour reperfusion period. The third group {6 saline-treated mice (Group 3A) and 6 CM101-treated mice (Group 3B)} was subject to occlusion for 60 minutes followed by reperfusion for 6 hours.

In the saline-treated mice, histological examination of the saline-treated kidneys revealed signs of reperfusion damage, showing greater injury with increased reperfusion time. Thus, damage to capillaries was evident after 2 hours of reperfusion (Group 1A) and evidence of angiogenesis, hemorrhage, and inflammation was observed in the 6-hour reperfusion mice (Group 3A). Additionally, cell death was observed by 4 hours (Group 2A). By contrast, at all time points the CM101-treated mice showed minor dilation of blood vessels, but no hemorrhaging between blood vessels, inflammation, or cell death. This demonstrates the protective role of CM101 in ischemia and reperfusion injury.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of protecting against reperfusion injury in a patient, which method comprises:

administering a polysaccharide toxin from group B β-hemolytic Streptococcus (GBS) bacteria to the patient prior to reperfusion of a blood vessel, wherein the GBS toxin has a molecular weight of approximately 300,000 Daltons and comprises N-acetyl-galactosamine, N-acetyl-glucosamine, glucose, galactose, and mannose residues in an approximate 1:1:1:3:1 ratio.

2. The method of claim 1 wherein the GBS toxin is administered prior to occlusion of the blood vessel.

3. The method of claim 1 wherein the GBS toxin has a purity of at least approximately 90%.

4. The method of claim 1 wherein the GBS toxin is administered to the patient in a quantity sufficient to reduce vascularization at the site of the reperfusion of the blood vessel.

5. A method of protecting a tissue or organ against reperfusion injury in a transplant patient, which method comprises:

administering a polysaccharide toxin from group B β-hemolytic Streptococcus (GBS) bacteria to the transplant patient prior to occlusion of a blood vessel, wherein the GBS toxin has a molecular weight of approximately 300,000 Daltons and comprises N-acetyl-galactosamine, N-acetyl-glucosamine, glucose, galactose, and mannose residues in an approximate 1:1:1:3:1 ratio.

6. The method of claim 5, which method further comprises:

administering the GBS toxin to the transplant patient prior to reperfusion of the blood vessel.

7. The method of claim 5 wherein the GBS toxin is administered to the transplant patient in a quantity sufficient to reduce vascularization at the site of the reperfusion of the blood vessel.

8. A method of protecting a transplanted organ against reperfusion injury in a transplant patient, which method comprises:

administering a polysaccharide toxin from group B β-hemolytic Streptococcus (GBS) bacteria to the transplant patient, wherein the GBS toxin has a molecular weight of approximately 300,000 Daltons and comprises N-acetyl-galactosamine, N-acetyl-glucosamine, glucose, galactose, and mannose residues in an approximate 1:1:1:3:1 ratio.

9. The method of claim 8, wherein administering the GBS toxin to the transplant patient occurs prior to occlusion of a blood vessel.

10. The method of claim 8, wherein administering the GBS toxin to the transplant patient occurs at the time of reperfusion of the transplanted organ.

11. The method of claim 10 wherein the GBS toxin is administered to the transplant patient in a quantity sufficient to reduce vascularization at the site of the reperfusion of the blood vessel.

12. A method of protecting against reperfusion injury in a patient, which method comprises:

administering CM101 to the patient prior to reperfusion of a blood vessel.

13. The method of claim 12 wherein the CM101 is administered prior to occlusion of the blood vessel.

14. The method of claim 12 wherein the CM101 has a purity of at least approximately 90%.

15. The method of claim 12 wherein the CM101 is administered to the patient in a quantity sufficient to reduce vascularization at the site of the reperfusion of the blood vessel.

16. A method of protecting a tissue or organ against reperfusion injury in a transplant patient, which method comprises:

administering CM101 to the transplant patient prior to occlusion of a blood vessel.

17. The method of claim 16, which method further comprises:

administering the CM101 to the transplant patient prior to reperfusion of the blood vessel.

18. The method of claim 16 wherein the CM101 is administered to the transplant patient in a quantity sufficient to reduce vascularization at the site of the reperfusion of the blood vessel.

19. A method of protecting a transplanted organ against reperfusion injury in a transplant patient, which method comprises:

administering CM101 to the transplant patient.

20. The method of claim 19, wherein administering the CM101 to the transplant patient occurs prior to occlusion of a blood vessel.

21. The method of claim 19, wherein administering the CM101 to the transplant patient occurs at the time of reperfusion of the transplanted organ.

22. The method of claim 21 wherein the CM101 is administered to the transplant patient in a quantity sufficient to reduce vascularization at the site of the reperfusion of the blood vessel.

* * * * *